United States Patent [19]
Albrecht et al.

[11] Patent Number: 5,305,079
[45] Date of Patent: Apr. 19, 1994

[54] NONDESTRUCTIVE METHOD FOR DETECTING DEFECTS IN THIN FILM USING SCATTERED LIGHT

[75] Inventors: Otto Albrecht, Atsugi; Ken Eguchi, Yokohama, both of Japan

[73] Assignee: Canon Kabushiki Kaisha, Tokyo, Japan

[21] Appl. No.: 901,160

[22] Filed: Jun. 19, 1992

[30] Foreign Application Priority Data

Jun. 24, 1991 [JP] Japan .................... 3-178686

[51] Int. Cl.⁵ ............................................ G01N 21/88
[52] U.S. Cl. .................................................... 356/237
[58] Field of Search ............................ 356/239, 237

[56] References Cited

U.S. PATENT DOCUMENTS

| | | | |
|---|---|---|---|
| 3,782,836 | 1/1974 | Fey et al. | 356/237 X |
| 4,297,032 | 10/1981 | Temple | 356/239 X |
| 4,449,818 | 5/1984 | Yamaguchi et al. | 356/237 |
| 4,469,442 | 9/1984 | Reich | 356/237 X |
| 4,966,455 | 10/1990 | Avni et al. | 356/73 |
| 4,966,457 | 10/1990 | Hayano et al. | 356/237 |

FOREIGN PATENT DOCUMENTS

| | | | |
|---|---|---|---|
| 0204071 | 12/1986 | European Pat. Off. | G01N 21/88 |
| 4-132942 | 5/1992 | Japan | 356/237 |
| 2111200 | 6/1983 | United Kingdom | G01N 21/88 |

OTHER PUBLICATIONS

IBM Journal of Research And Development, vol. 26, No. 2, Mar. 1982, New York, pp. 209-216, J. F. Rabolt et al., "Integrated optics and raman scattering: Molecular orientation in thin polymer films and Langmuir-Blodgett monolayers".

Patent Abstracts of Japan, vol. 013, No. 474 (E-836), Oct. 26, 1989 & JP-A01 185 934 (Hitachi) Jul. 25, 1989.
G. L. Larkins et al., "Langmuir-Blodgett Films As Barrier Layers In Josephson Tunnel Junctions," Thin Solid Films, vol. 99, No. 1/2/3, Jan. 14, 1983, pp. 277-282.
G. G. Roberts et al., "GaP Phthalocyanine Langmuir-Blodgett Film Electroluminescent," Electronics Letters, vol. 20, No. 12, Jun. 7, 1984, pp. 489-491.
N. J. Thomas et al., "GaAs/LB Film Miss Switching Device," Electronics Letters, vol. 20, No. 20, Sep. 27, 1984, pp. 838-839.
I. R. Peterson, "Defect Density in a Metal-Monolayer-Metal Cell," Australian Journal of Chemistry, vol. 33, No. 8, Aug. 1980, pp. 1713-1716.
P. Lesieur, "Defect Characterization And Detection In Langmuir-Blodgett Films," Thin Solid Films, vol. 152, No. 1, Sep. 14, 1987, pp. 155-165.
I. R. Peterson, "A Structural Study of the Conducting Defects in Fatty Acid Langmuir-Blodgett Monolayers," Journal of Molecular Electronics, vol. 2, 1986, pp. 95-99.

*Primary Examiner*—Vincent P. McGraw
*Attorney, Agent, or Firm*—Fitzpatrick, Cella, Harper & Scinto

[57] ABSTRACT

A method for detecting defects in a film structure of a thin film formed on a substrate by projecting a light flux in a direction precisely parallel or nearly parallel to the face of the substrate, separating a reflected light from the thin film and the substrate from a scattered light in a direction precisely perpendicular or nearly perpendicular to the face of the substrate and reading information only of the scattered light.

6 Claims, 3 Drawing Sheets

200μm

1

NONDESTRUCTIVE METHOD FOR DETECTING DEFECTS IN THIN FILM USING SCATTERED LIGHT

BACKGROUND OF THE INVENTION

1. Field of the Invention

The present invention relates to a method for testing a thin film structure, particularly to a method for testing a state of a thin film structure by detecting a structural defect, such as a pinhole, in the formed thin film by utilizing scattered light which is caused by the defect when light flux is projected to the defect.

2. Related Background Art

Recently, the ordered structure of organic materials (or organic molecules) has come to be noticed in connection with development and improvement in electronic functions. In particular, electronic devices employing organic molecules are attracting attention.

As for the techniques of constructing molecular electronic devices, many reports have been disclosed regarding Langmuir-Blodgett films (LB films).

An LB film is constituted of a regular lamination of monomolecular layers of an organic compound. The LB film has enabled formation of a uniform ultra-thin film by controlling the film thickness thereof in the order of the unit of a molecular length. Many attempts have been made to use the LB film as an insulator.

Examples of the attempts include a tunnel junction element having a structure of metal/insulator/metal (MIM) [G. L. Larkins, et al.: "Thin Solid Films", Vol. 99 (1983)]; a light-emitting element having a structure of metal/insulator/semiconductor (MIS) [G. C. Roberts, et al.: Electronics Letters, Vol. 20, p. 489 (1984)]; and a switching element [N. J. Thomas, et al.: Electronics Letters, Vol. 20, p. 838 (1984)].

Even after the investigations of characteristics of the elements in these studies, the problems still remain unsolved such as variation of the properties of respective elements and deterioration by aging thereof which are considered to be ascribable to structural defects in LB films, causing lack of reproducibility and of stability.

One of the problems in detection of a structural defect of an LB film, is that the structural defect of the LB film is required to be visualized and to be numerically evaluated within a limited time.

In conventional evaluation, the results are shown as indirect and average data such as in a copper metallizing process [I. R. Peterson: Aust. J. Chem., Vol. 33, p. 173 (1980)]; and measurement of electroconductivity for an MIM structure [P. Lesieur, et al.: Thin Solid Films, Vol. 152, p. 155 (1987), and I. R. Peterson: J. Mol. Electron., Vol. 2, p. 95 (1986)].

Further, the evaluation by electron microscopy is complicated for the evaluation of structural defects of an LB film because many parameters have to be controlled to obtain significant results. Therefore, the electron microscopy requires technical skill as well as much time for the measurement.

SUMMARY OF THE INVENTION

The present invention intends to provide a method for detecting structural defects of an organic thin film such as an LB film quickly and with high precision by a simple apparatus in air.

The present invention provides a method for detecting defects in a film structure of a thin film formed on a substrate, comprising projecting a light flux in a direction precisely parallel or nearly parallel to the face of the substrate; separating a reflected light from the thin film and the substrate from a scattered light toward the direction precisely perpendicular or nearly perpendicular to the face of the substrate; and reading information only of the scattered light.

DESCRIPTION OF THE PREFERRED EMBODIMENT

Figure 1:
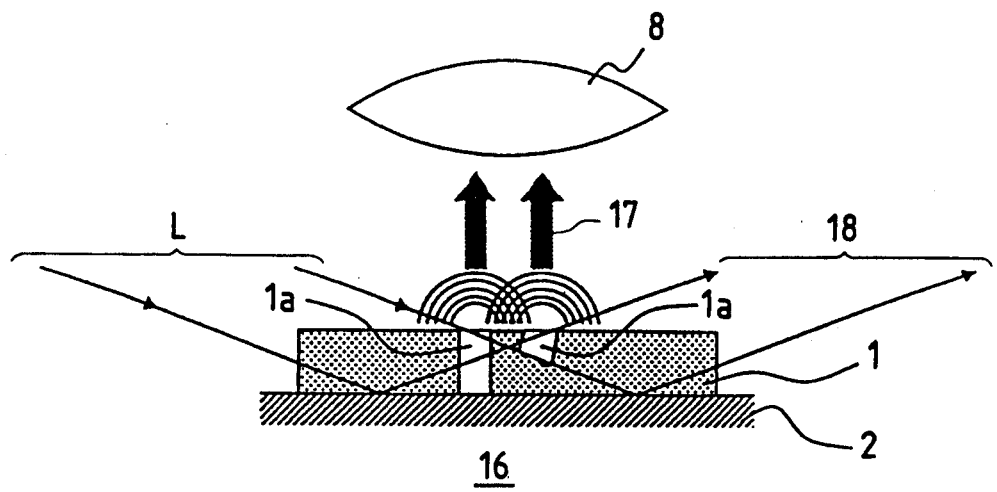
FIG. 1 illustrates schematically the principle of the detection of defects in structure of a thin film in the present invention.

FIG. 1 illustrates schematically the principle of the detection of defects in structure of a thin film in the present invention. A flat thin film 1 in the drawing is made of an organic material. The organic thin film as the object of the present invention has generally a thickness of from several ten Å to several thousand Å. In particular in the case where the thin film is an LB film, the thickness is in the range of from several Å to thousand Å, preferably from 4 Å to 1000 Å, more preferably from 50 Å to 100 Å as the object of evaluation of the film. A minute defect 1a like a pinhole inside the organic thin film are also shown schematically in FIG. 1.

A specimen 16 is constituted of a flat substrate 2 and an organic thin film 1 formed thereon. A light flux (a projected light) L is projected from a light source (not shown in the drawing) such as a laser source to the substrate 2 in a direction precisely parallel or nearly parallel to the substrate 2. If the organic thin film 1 is uniform and has no defect in the internal structure of the thin film 1, the introduced light flux L is simply transmitted through the organic thin film 1, or transmitted through the thin film 1 and then reflected by the substrate 2, thus the reflected light is ejected from the other end.

On the contrary, if the organic thin film involves a defect 1a like a pinhole inside, the light flux L introduced to the defect 1a is scattered by the defect 1a. That is, the light flux L is scattered by the change of the refractive index resulting from the defect 1a, and the scattered light is ejected in various directions.

Among various directions of a scattered light caused by the defect 1a, the scattered light 17 directed precisely or nearly perpendicular to the substrate 2 is collected by a condensor lens (or an objective) 8, and an image of the thin film structure of the organic thin film 1 caused by the scattered light 17 is formed on a plane of an imaging means such as a CCD (not shown in the drawing).

As described above in the present invention, the light flux L is projected in a direction parallel or nearly parallel to the organic thin film 1, whereby the light which is transmitted simply through the thin film 1 and the regular reflection light 18 which is reflected regularly by the substrate 2 are not introduced to the condensor lens 8.

The image of the scattered light caused by defects in the thin film structure and formed by an imaging means is subjected to image analysis with an image-processing means (not shown in the drawing), thereby the structural defects in organic thin films being detected.

Figure 2:
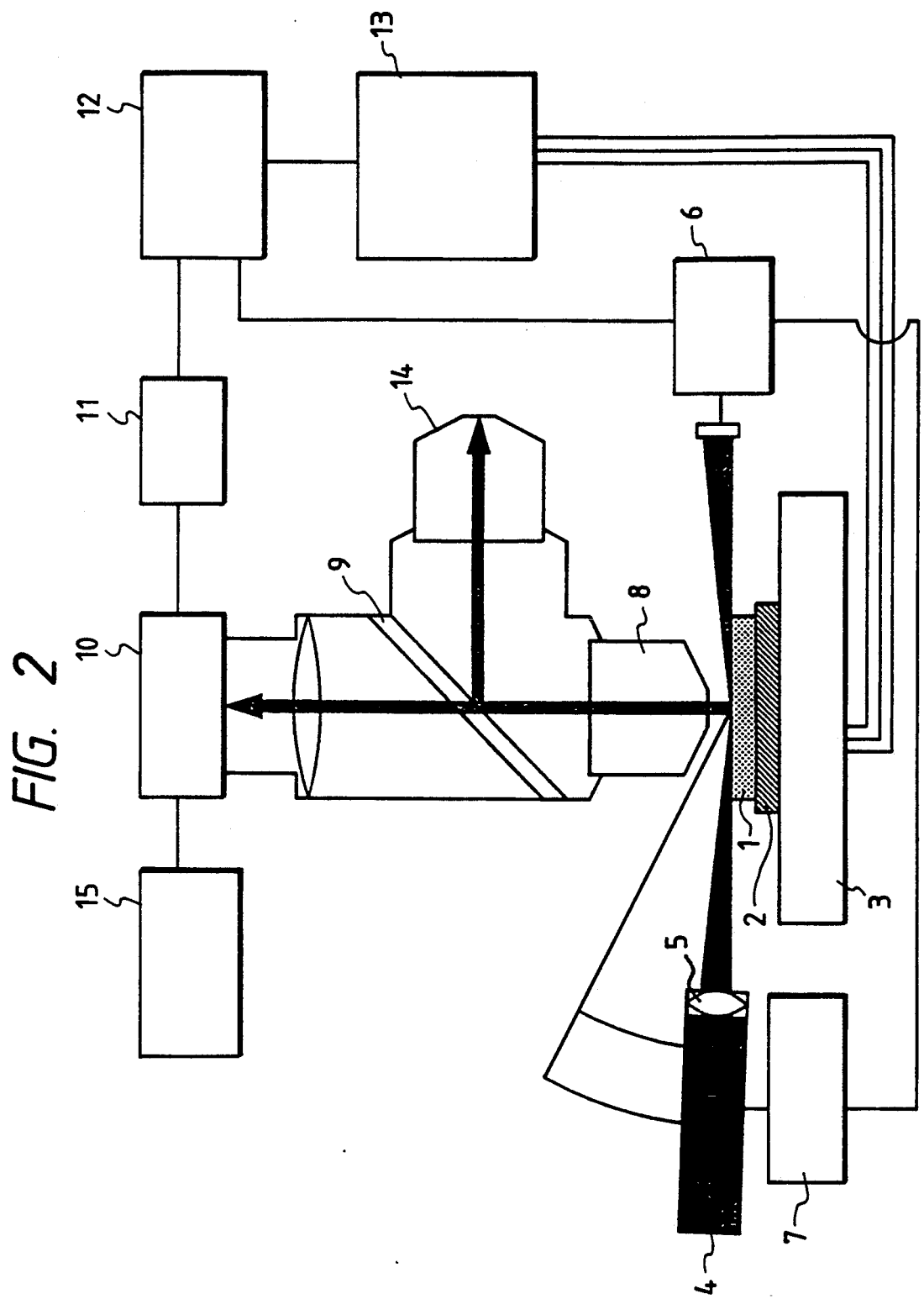
FIG. 2 illustrates schematically a apparatus for detecting a defect in structure of an organic thin film by the method of the present invention.

FIG. 2 illustrates schematically an apparatus for detecting a defect in structure of an organic thin film by the method of the present invention. In this example, an optical microscope system is applied to the present invention.

The construction of this example causes no trouble in functions of the optical microscope system such as a light source for observation, a polarizer plate, an analyzer plate, a camera, and so forth. In FIG. 2, the flat organic thin film 1 is formed on an optically flat substrate 2.

A support 3 is constructed of an XYZ three-axis stage which is movable in an XY plane and in a Z axis direction. A substrate 2 having an organic thin film 1 is placed on the support. A light source means 4 comprises an LED or a laser source. A light-projecting means 5 converges the light flux from the light source means 4, and projects the light as fine flux to the organic thin film 1 in a direction parallel or nearly parallel to the substrate 2. The light source means 4 and the light-projecting means 5 are integrated into one body, and are provided with a position control device for projecting light flux in a direction parallel or nearly parallel to the organic thin film. The light source means 4 and the light-projecting means 5 are constructed in one body, for example, so as to be rotatable around the centor of the support 3.

A photosensor 6 monitors the variation of light output from the light source means 4 by detecting the light flux having passed through the organic thin film 1, or the light flux of both having passed through the organic thin film and having seen regularly reflected by the substrate 2.

That is, the light output from the light source means 4 is stabilized by inputting the output signal from the photosensor 6 to the stabilized power source 7. Thereby image information obtained by an optical area sensor 10, which is an imaging means described later, is standardized to facilitate comparison of organic thin films to be tested.

An objective 8 concentrates the scattered light caused by a structural defect in a direction perpendicular or nearly perpendicular to the organic thin film 1, and introduces the light through a half mirror 9 to an optical area sensor 10 at a predetermined magnification to form image information thereon regarding the structural defects of the organic thin film 1. In the optical area sensor 10, an image is formed as a bright spot caused by scattered light from the defect in the organic thin film 1 as shown in drawings shown later.

The optical area sensor 10 converts image information regarding the organic thin film 1 into an electric image data. The sensitivity of the optical area sensor 10 is optimized by an optimizing circuit 15 so as to carry out digital treatment effectively. The image data from the optical area sensor 10 is digitalized by an A/D converter 11, and is inputted to an image-processing means 12, where the electric signal is converted to a numerical signal. The image signal, after being processed by the image-processing means 12, is inputted to a computer 13. The computer 13 analyzes the image signal from the image-processing means 12, thereby characterizing the structural defect of the organic thin film 1.

The computer 13 controls the movement of the support 3 three-dimensionally (in XYZ directions), thereby enabling automatic observation such as automatic focusing, and automatic positional measurement of density of structural defects.

With an ocular 14, the state of the structural defects is observed by utilizing the scattered light, which is caused by structural defects of the organic thin film 1, through the objective 8 and the half mirror 9.

In this example constituted as above, defects in the organic thin film 1 like a pinhole are detected as image information, and the presence of structural defects of organic thin films is inspected with high accuracy.

Figure 3:
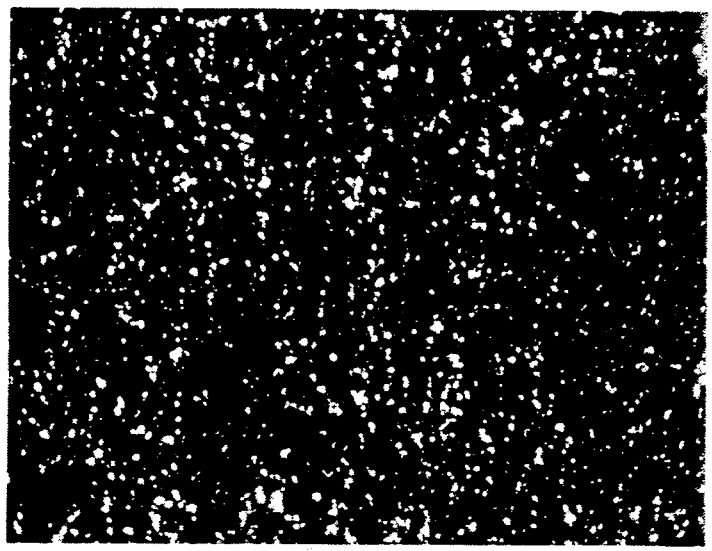
FIG. 3 is an photographic image of defects of a fatty acid LB film obtained by use of an apparatus employing the method of the present invention.

FIG. 3 is a photographic image of defects in a fatty acid LB film obtained by use of an apparatus employing the method of the present invention.

Figure 4:
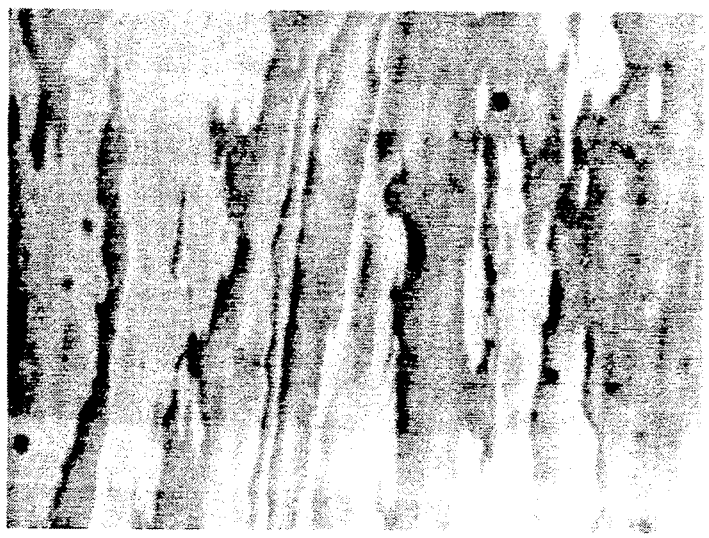
FIG. 4 is a polarizing microscopic image of a fatty acid LB film.

FIG. 4 is a polarizing microscopic image of the same fatty acid LB film taken by means of a conventional optical microscope, for reference.

In FIG. 3, the white spots show structural defects such as pinholes.

The present invention enables clear detection of structural defects of an organic thin film as shown in FIG. 3, and allows detection of structural defect and evaluation of an organic thin film with high accuracy in comparison with the photograph obtained with a conventional optical microscope as shown in FIG. 4.

Figure 5:
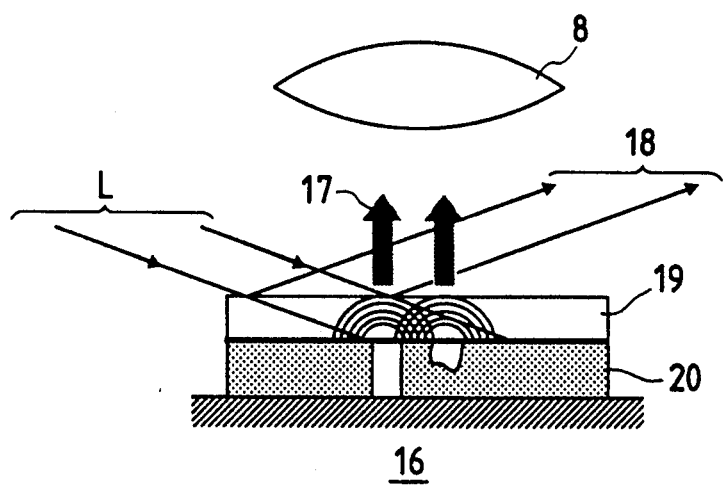
FIG. 5 illustrates schematically the principle of the detection of the structure at and around of an interface of a thin film in the present invention.

FIG. 5 illustrates another evaluation method employing a method of detecting defects in a thin film of the present invention. A first medium 19 has a higher refractive index than a second medium 20. The light flux that is introduced at an angle of incidence corresponding to the critical angle which depends on the refractive indexes of the both mediums 19 and 20 is confined by the interface 19/20 without leaking out of the surface. If the refractive index changes at or around the interface, the light is not confined by the interface any more, coming out through the surface. Accordingly, in the same manner as described by reference to FIG. 1, distribution of refractive index around the interface of the medium 20 (or the medium 19) can be shown imagewise by collecting the component of light in a perpendicular or nearly perpendicular direction. Moreover, use of polarized light as the projecting light enables detailed analysis of information on anisotropy at the interface. In other words, the method of the present invention, when applied to the construction as shown in FIG. 5, enables detecting structural defects scattered around the interface with high sensitivity, even if an area of each structural defect is minute.

As described above, the present invention provides a method for detecting a structural defect such as a film-lacking portion (like a pinhole) in a simple manner.

The method of the present invention is applicable not only to a defect which pierces through a film like the defect 1a at the left side in FIG. 1, but also to a defect which is localized near an interface like the defect 1a at the right side of FIG. 1.

The present invention enables visualization of a structural defect of an organic thin film (structural change which causes change of refractive index to incident light) in a simple manner as with a conventional optical microscope in air. Further the present invention enables image analysis to analyse a density of defect and the distribution thereof, a size of defect and the distribution thereof, further a correlation of a distribution of defect with that of domain, and so forth.

The present invention provides a method for testing and evaluating the quality of a thin film structure, especially of an organic thin film quickly with high precision in a simple manner in the air by setting the elements as described above. The present invention also provides a method for testing the interfacial structure of a thin film.

The testing method and the testing apparatus of the present invention are applicable widely to evaluation of a state of a film such as an LB film and a liquid crystal film.

What is claimed is:

1. A method for detecting defects in a film structure of a thin film formed on a substrate, comprising the steps of:

projecting a light flux in a direction precisely parallel or substantially parallel to the face of the substrate:

separating a reflected light from the thin film and the substrate from a scattered light caused by a defect in said thin film;

collecting the scattered light toward the direction precisely perpendicular or substantially perpendicular to the face of the substrate and introducing said collected scattered light into an imaging means; and reading information only of said collected scattered light.

2. The method according to claim 1, wherein the thickness of said thin film is in the range of from several ten Å to several thousand Å.

3. The method according to claim 1, wherein said thin film is an LB film.

4. The method according to claim 3, wherein the thickness of said LB film is in the range of from several Å to thousand Å.

5. The method according to claim 4, wherein the thickness of said LB film is in the range of from 4 Å to 1,000 Å.

6. The method according to claim 4, wherein the thickness of said LB film is in the range of from 50 Å to 1,000 Å.

* * * * *